(12) United States Patent
Porter

(10) Patent No.: US 8,747,430 B2
(45) Date of Patent: Jun. 10, 2014

(54) DEVICE FOR CLOSURE OF A VASCULAR DEFECT AND METHOD FOR TREATING THE SAME

(75) Inventor: Stephen Porter, Fremont, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 1531 days.

(21) Appl. No.: 11/433,280

(22) Filed: May 12, 2006

(65) Prior Publication Data

US 2006/0206196 A1 Sep. 14, 2006

Related U.S. Application Data

(62) Division of application No. 10/230,803, filed on Aug. 29, 2002, now abandoned.

(51) Int. Cl.
*A61M 29/00* (2006.01)

(52) U.S. Cl.
USPC .......................................... 606/200; 623/1.11

(58) Field of Classification Search
USPC .......................................... 606/200; 623/1.11
See application file for complete search history.

(56) References Cited

U.S. PATENT DOCUMENTS

| | | | |
|---|---|---|---|
| 6,063,111 A | 5/2000 | Hieshima et al. | |
| 6,168,592 B1 | 1/2001 | Kupiecki et al. | |
| 6,210,429 B1 * | 4/2001 | Vardi et al. | 623/1.11 |
| 6,361,558 B1 | 3/2002 | Hieshima et al. | |
| 6,602,261 B2 * | 8/2003 | Greene et al. | 606/108 |
| 6,790,218 B2 | 9/2004 | Jayaraman | 606/191 |
| 6,802,851 B2 * | 10/2004 | Jones et al. | 606/200 |
| 6,811,560 B2 | 11/2004 | Jones et al. | |
| 6,827,736 B2 * | 12/2004 | Perouse | 623/1.36 |
| 7,306,622 B2 | 12/2007 | Jones et al. | |
| 2005/0251200 A1 | 11/2005 | Porter | 606/200 |

OTHER PUBLICATIONS

U.S. Appl. No. 10/230,803, filed Aug. 29, 2002, Porter.

* cited by examiner

*Primary Examiner* — Darwin Erezo
*Assistant Examiner* — Diane Yabut
(74) *Attorney, Agent, or Firm* — Vista IP Law Group LLP

(57) ABSTRACT

A device for the non-invasive treatment of a vascular defect. The device includes at least one occlusive member having a first unexpanded configuration and a second expanded configuration and at least one securement member for securing the vaso-occlusive device to a support structure at the location of the vascular defect.

19 Claims, 6 Drawing Sheets

DEVICE FOR CLOSURE OF A VASCULAR DEFECT AND METHOD FOR TREATING THE SAME

CROSS-REFERENCE TO RELATED APPLICATIONS

This application is a divisional of U.S. patent application Ser. No. 10/230,803, filed Aug. 29, 2002, now abandoned the entire content of which is incorporated by reference

FIELD OF THE INVENTION

The present invention relates generally to implantable devices and methods for the treatment of vascular defects.

BACKGROUND OF THE INVENTION

Many minimally invasive or noninvasive interventional medical devices and procedures have been used to treat defects in the vasculature which are not easily reached by surgical procedures. Such medical devices which are adapted for implantation in body lumens in order to support weakened or occluded vessel walls and allow fluid flow are well known and commercially available. One such device is a vascular stent, for example. Stents may be employed to prop up vessel walls and maintain openings in vessels in the coronary system, the brain, the urinary, biliary, esophageal, tracheal and bronchial tracts, and so forth.

However, in some situations, it is desirable to block fluid flow. For example, one serious defect in the vascular system is an aneurysm which is an area of a weakened vessel wall that causes a bulge or bubble to protrude out in a radial direction from the adjacent vessel. If untreated, an aneurysm may continue expanding until it bursts, causing hemorrhage. It is therefore often desirable to block fluid flow to the aneurysm.

Devices used for the treatment of such defects may be referred to as vaso-occlusive devices and are commonly deployed to the aneurysm site through the use of a catheter device. Vaso-occlusive devices can have a variety of configurations, and are generally formed of one or more elements that have a deployed configuration for blocking blood flow which is different from their configuration during delivery to the site.

Devices for bridging the necks of wide-necked or narrow-necked aneurysms are found, for example, in U.S. Pat. No. 5,935,148, U.S. Pat. No. 6,063,070, U.S. Pat. No. 6,036,720, U.S. Pat. No. 6,063,104 and U.S. Pat. No. 6,139,564. These devices may also be used to stabilize the placement of vaso-occlusive devices such as helically wound coils in the aneurysm or may be used to, at least partially, close the aneurysm neck. The aneurysm neck bridge or retainer assemblies described in the patents above may be delivered to the aneurysm in a variety of different ways, but preferably are attached to an electrolytically severable joint for their deployment. After deployment of the neck bridge or retainer, the aneurysm is at least partially filled with a vaso-occlusive device such as a helically wound coil. The vaso-occlusive devices may also be delivered to the aneurysm using a number of different methods such as by a core wire which is linked to the coils by an electrolytically severable joint or a mechanically severable joint. The vaso-occlusive devices may also be simply pushed into the aneurysm. The success of such devices as those described above, may depend on several factors, however, including whether or not the device can migrate out of the aneurysm through the neck of the aneurysm.

Another example of a vaso-occlusive device applicable to the treatment of an aneurysm is a covered stent or a stent-graft. Covered stents have a limited usefulness due to the stiffness of the device, and synthetic grafts themselves have a tendency to occlude when employed in small blood vessels. Arteries where there is an aneurysm typically have a lot of branching, and when employing a covered stent, there is a further risk of occluding the small branch vessels airising from the parent artery rather than simply blocking the neck of the aneurysm as desired.

Thus, it would be beneficial to have a vaso-occlusive device that can be delivered to an aneurysm or other body vessel in a primary unexpanded configuration, wherein such device can be deployed and released to assume a secondary, expanded configuration which occludes the neck of the aneurysm, and which can be anchored at the site of the aneurysm so that it does not migrate from the site.

SUMMARY OF THE INVENTION

The present invention relates generally to a vaso-occlusive device which is adapted to be inserted into a portion of a vasculature for treatment of a body vessel such as an aneurysm, and to methods of using the device. The vaso-occlusive device of the present invention is generally employed in combination with a support structure such as a stent, stent-graft, and the like. The device is designed in such a way that it may be readily anchored at the site of the vascular defect to prevent migration of the device. Of course, more than one support structure may be employed in a given procedure as well.

The vaso-occlusive device of the present invention includes at least one occlusive member having a first unexpanded configuration and a second expanded configuration, and at least one securement member for securing the device to a stent, stent-graft, or the like, in order to prevent migration of the fluid flow-occluding device from the site of the vascular defect.

The device is retained within or as a part of a microcatheter system in an unexpanded configuration to cross the neck of the aneurysm, and then once across the neck, the device may be allowed to expand by pulling back the microcatheter, pulling back a shaft about the microcatheter, or by employing a pusher device.

The device may be formed of a variety of materials including, but not limited to flexible polymeric materials and metallic materials including shape memory materials, superelastic materials, compressed foams, swellable materials, braided or woven materials and meshes formed from both polymeric materials and shape memory alloys, for example, and so forth. Suitably, the materials are biocompatible.

Bioactive materials or materials having incorporated bioactive agents may also be employed in the construction of the device according to the present invention.

The device may be employed in minimally invasive, interventional procedures for the treatment of a vascular defect where it is desirable to block the flow of fluid, if not completely then to a substantial degree, into the defective area of the vessel.

In one embodiment, the method includes deploying a support structure to the site of the vascular defect, deploying the vaso-occlusive device to the site of the vascular defect, inserting the vaso-occlusive device into the vascular defect through an opening in the support structure, deploying at least one occlusive member, and deploying at least one securement member.

Suitably, both the support structure and the vaso-occlusive device are deployed using a catheter.

These and other aspects and advantages of the invention will become apparent from the following detailed description and the accompanying drawings, which illustrate by way of example the features of the invention.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

Figure 1:
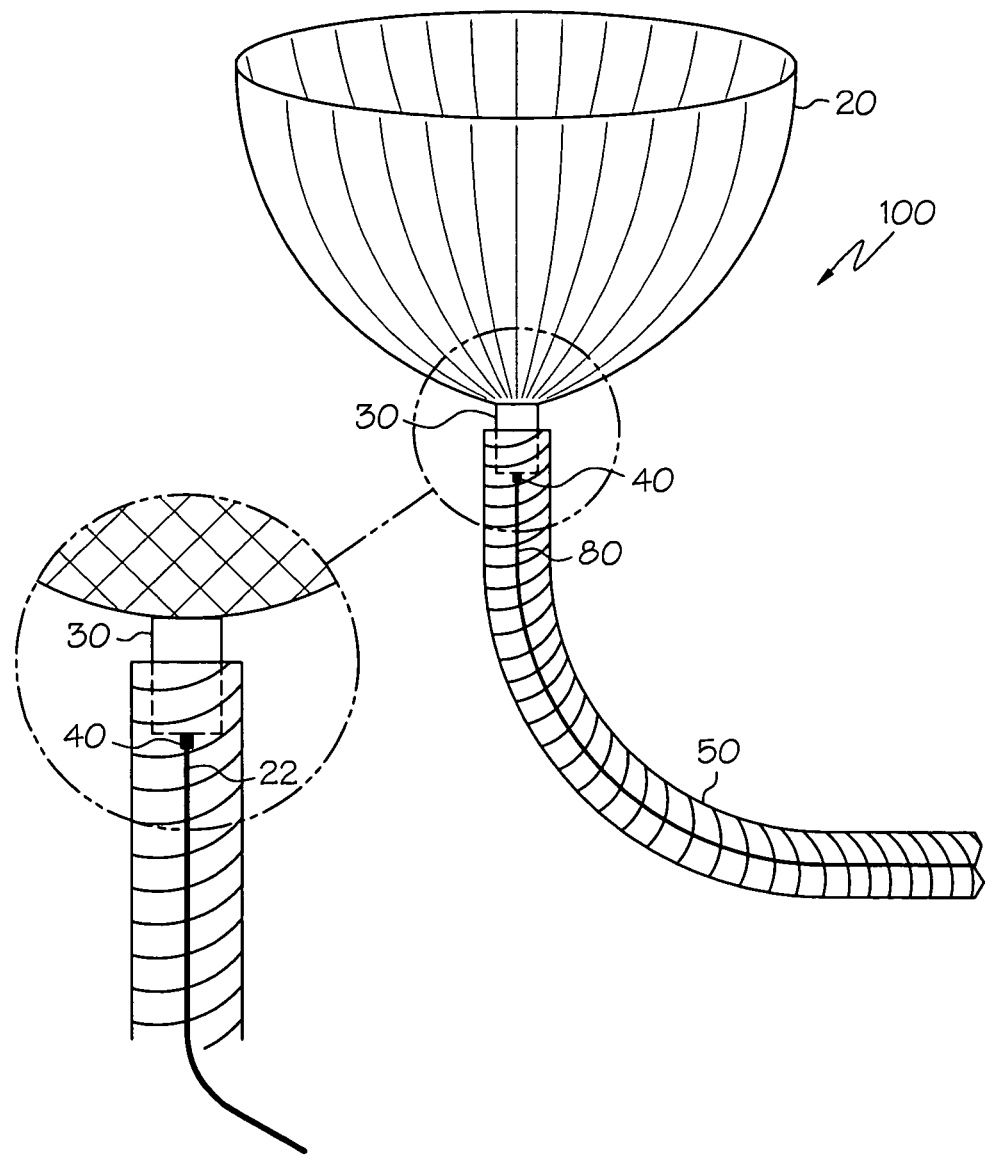
FIG. 1 illustrates one embodiment of a vaso-occlusive device according to the present invention.
Figure 2:
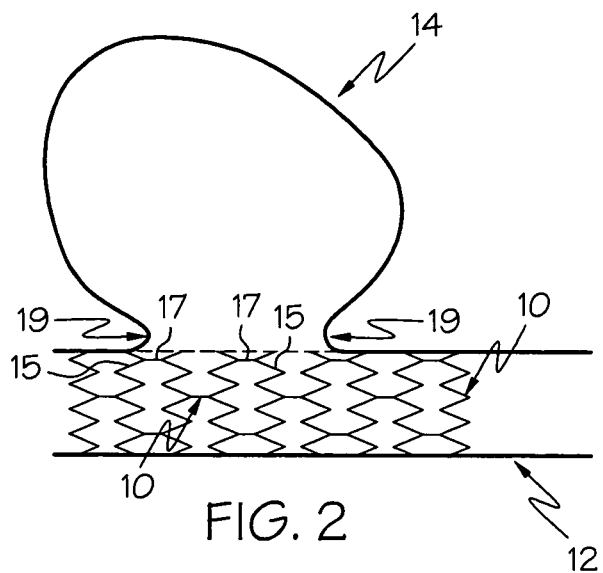
FIG. 2 is a depiction of a stent located in a blood vessel at the site of an aneurysm prior to deployment of a vaso-occlusive device according to the present invention.

Turning now to the figures, FIG. 1 illustrates generally at 100, one embodiment of the vaso-occlusive device according to the present invention in which the occlusive member 20 is in a fully expanded form, but the securement member 30 has not yet been released from the catheter 50. The top of the securement member 30 is visible. A pusher wire 22 is shown disposed within the catheter lumen.

Also seen in FIG. 1 is a severable junction 40 for severing the connection between a catheter delivery device 50 and the vaso-occlusive device 100 after deployment of vaso-occlusive device 100. Junction 40 may be severed using any of a variety of different methods including, but not limited to, electrolytic corrosion, mechanical actuation, hydraulic pressure, thermal processes, electromagnetic energy, and so forth as described above. Other methods of detachment known to those of skill in the art but not described herein may also be employed in releasing the device of the present invention. Severable junctions which may be employed in the present invention are described, for example, in U.S. Pat. No. 5,122,136, U.S. Pat. No. 5,354,295, U.S. Pat. No. 5,540,680, U.S. Pat. No. 5,855,578, U.S. Pat. No. 5,895,385, U.S. Pat. No. 5,925,037, U.S. Pat. No. 5,944,714, U.S. Pat. No. 5,947,963, U.S. Pat. No. 5,976,126, U.S. Pat. No. 6,010,498, U.S. Pat. No. 6,066,133 and U.S. Pat. No. 6,083,220, each of which is incorporated by reference herein in its entirety.

FIGS. 2-7 illustrate a series of steps involved in the deployment of the vaso-occlusive device 100 according to the present invention. Beginning with FIG. 2, a support structure, in this embodiment a stent 10, is shown deployed within a blood vessel 12 at the site of a vessel defect or aneurysm 14 and located at the opening or neck 19 of the aneurysm 14. The stent 10 has a plurality of stent struts 15 having openings 17 therebetween. Stent 10 is in its expanded configuration within blood vessel 12. An occlusive device according to the present invention may be formed and configured such that it may be deployed through the openings 17 between struts 15.

While the above stent is shown for illustrative purposes only, it is important to note that any stent design may be employed herein.

Figure 3:
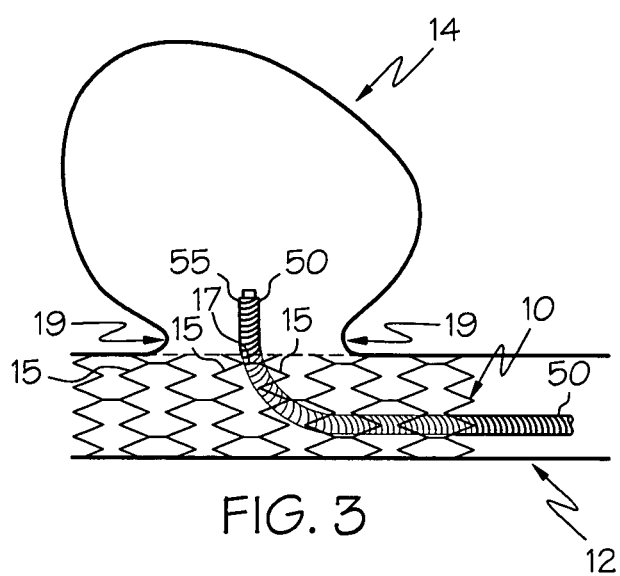
FIG. 3 illustrates initial delivery of a catheter device with the vaso-occlusive device of the present invention retained therein.
Figure 4:
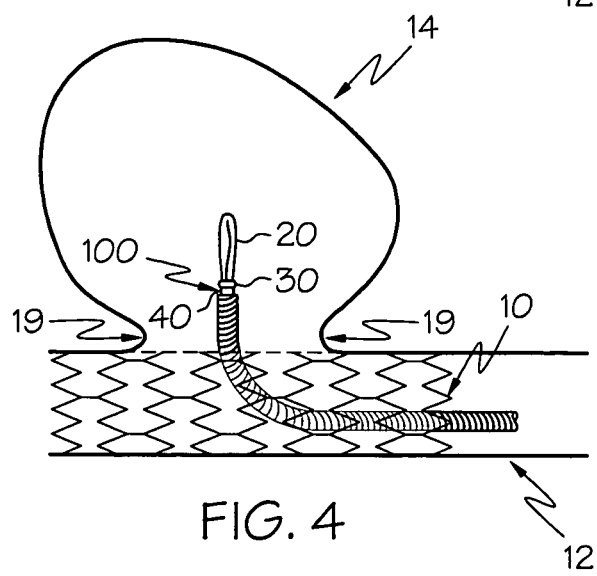
FIG. 4 illustrates initial deployment of the vaso-occlusive device released from the catheter but in an unexpanded state.

FIG. 3 illustrates the initial delivery of one embodiment of the device of the present invention (not visible in FIG. 2) in an unexpanded state through the use of a microcatheter device 50, such as a microcatheter. The microcatheter 50 is guided through blood vessel 12 and through stent 10 and is then threaded through an opening 17 located between stent struts 15 and into the aneurysm 14. The vaso-occlusive device 10 (not shown) may be rolled, compressed or otherwise unexpanded into a form that can be pushed through and retained in microcatheter 50. In FIG. 4, the microcatheter 50 can be seen shown disposed within stent 10 in blood vessel 12 and projecting upward through opening 17 formed by struts 15 and into aneurysm 14. The securement member 30 can be seen at the distal tip 55 of microcatheter 50.

In FIG. 4, vaso-occlusive device 100 is shown in the initial stage of being released from microcatheter 50 by use of a pusher wire 22 (not shown). The occlusive member 20 is still in an unexpanded configuration. The securement member 30 is also in its unexpanded configuration. Reference numeral 40 represents a detachable or severable junction which can be severed using a number of different mechanisms including, but not limited to, electrolytic corrosion, mechanical actuation, hydraulic pressure, thermal processes, electromagnetic energy, and so forth as described above. It is at this junction 40 that the vaso-occlusive device 100 is eventually detached from pusher wire 22 (not shown) which is disposed inside microcatheter 50. Other methods of detachment not described herein, but known in the art, may also be employed in detaching the device of the present invention.

As noted above, severable junctions are described, for example, in U.S. Pat. No. 5,122,136, U.S. Pat. No. 5,354,295, U.S. Pat. No. 5,540,680, U.S. Pat. No. 5,855,578, U.S. Pat. No. 5,895,385, U.S. Pat. No. 5,925,037, U.S. Pat. No. 5,944,714, U.S. Pat. No. 5,947,963, U.S. Pat. No. 5,976,126, U.S. Pat. No. 6,010,498, U.S. Pat. No. 6,066,133 and U.S. Pat. No. 6,083,220, each of which is incorporated by reference herein in its entirety.

Figure 5:
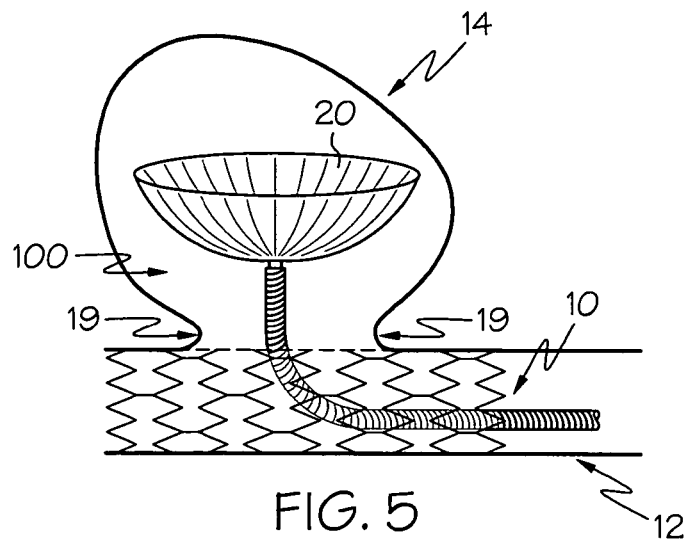
FIG. 5 illustrates one embodiment of the occlusive member of the vaso-occlusive device of the present invention in an expanded state.

Upon release from microcatheter 50, occlusive member 20 expands as shown in FIG. 5. Occlusive member 20 may be made expandable upon release using any number of methods known in the art. For example, shape memory materials including both polymeric and metallic materials may be employed, materials which are swellable in an aqueous environment may be employed, compressed foams, braided, woven, knit, felt-like materials, meshes, and so forth, may also be employed. In this particular embodiment, occlusive member 20 is shown in an umbrella-like form. However, occlusive member 20 may be in the form of a disc, parabola, sphere, or the like providing that it is of a configuration to block or bridge the neck 19 of aneurysm 14 so that no fluid, or substantially no fluid, may flow between vessel 12 and aneurysm 14. Suitable materials for formation of such an occlusive member include flexible polymeric materials, for example. Securement member 30, is also not yet in its deployed configuration.

Figure 6:
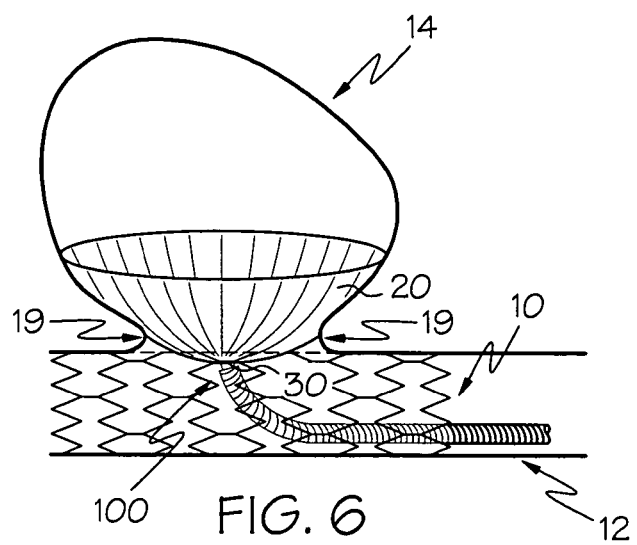
FIG. 6 illustrates one embodiment of the vaso-occlusive device of the present invention positioned at the neck of an aneurysm.

Occlusive member 20 is then pulled back until it comes in contact with stent 10 and is now blocking the opening or neck 19 of aneurysm 14 as shown in FIG. 6. At this point, securement member 30, is at least partially protruding through the opposite side of the stent struts 15 as the occlusive member 20, and is still in an unexpanded configuration.

Figure 7:
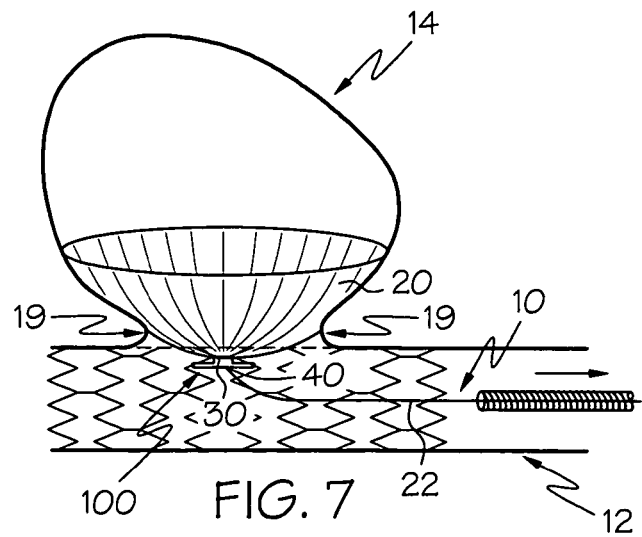
FIG. 7 illustrates one embodiment of the vaso-occlusive device of the present invention in an expanded state with the securement member released and in position.

The securement member 30 is then released by pulling back on the catheter device 50 while maintaining the position of the pusher wire 22 as shown in FIG. 7. The securement member 30 upon release from the catheter device 50 expands. In its expanded configuration, securement member 30 anchors the vaso-occlusive device 100 to the stent 10. The securement member 30 is located on the opposite side of the stent struts 15 as the occlusive member 20. Securement member 30 may operate in one of several different ways. Desirably, the securement member 30 operates by either expanding to the point at which it may no longer fit back through the opening 17 between stent struts 15 through which it initially came, or it may be constructed of a shape memory material, for example, that remains inside the microcatheter 50 until deployment of the occlusive member 20. Thus, it does not deploy until the occlusive member 20 is deployed.

In FIG. 7, the microcatheter 50 is shown being drawn away from the vaso-occlusive device, releasing the securement member 30 which then lays open and flat against the stent struts 15. The securement member 30 extends through and is located on the opposite side of the occlusive member 20 and effectively anchors the vaso-occlusive device 100 into position.

Figure 8:
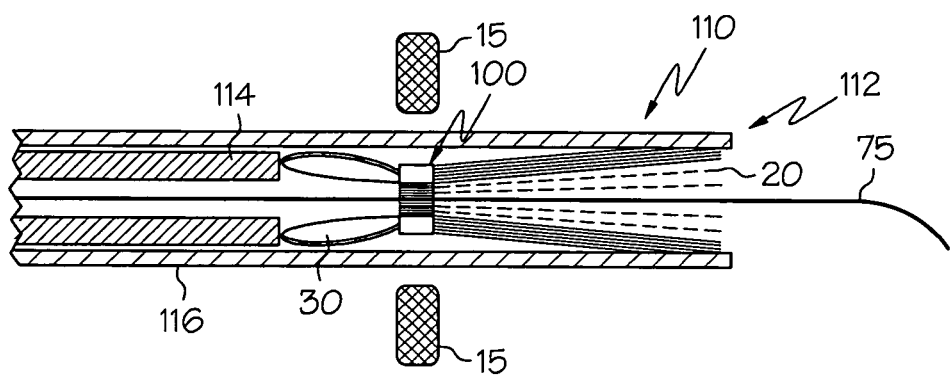
FIG. 8 illustrates a vaso-occlusive device according to the present invention, in combination with a catheter delivery device.

FIG. 8 illustrates generally at 110 a catheter delivery device having a vaso-occlusive device 100 disposed inside a retractable sheath 116 at the distal end 112 of the catheter delivery device 110. The catheter device has a tubular support structure 114. In this embodiment, a guidewire 75 is first positioned inside the vasculature. The catheter delivery device 110 is then maneuvered through the vasculature over the guidewire 75 to the site of the vascular defect (not shown) wherein a support structure such as a stent, has already been positioned. The catheter delivery device 110 is then maneuvered between struts 15 of the stent structure and is positioned in the vascular defect (not shown). In FIG. 8, the catheter delivery device 110 is shown positioned between two struts 15. The vaso-occlusive device is not yet deployed.

Figure 9:
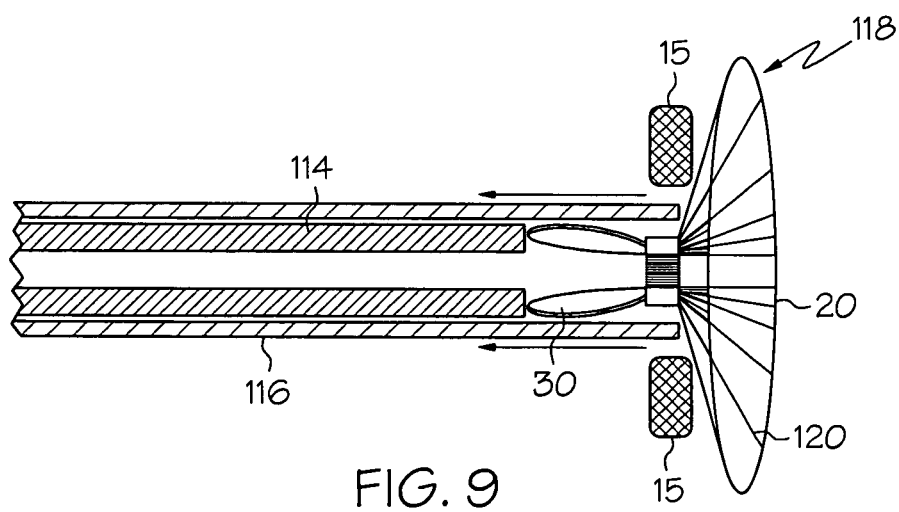
FIG. 9 illustrates the device of FIG. 8 during deployment.

In FIG. 9, the retractable sheath 116 is shown in a partially pulled back position releasing the occlusive member 20 of the vaso-occlusive device 100.

Figure 10:
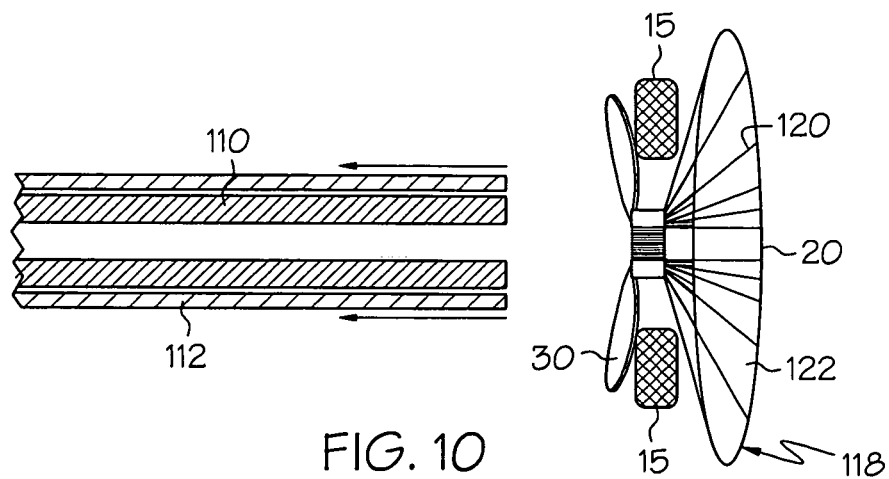
FIG. 10 illustrates the vaso-occlusive device of FIG. 8 after deployment.

In FIG. 10, the retractable sheath 116 has been pulled back all the way further releasing the securement member 30 of the vaso-occlusive device 100.

The vaso-occlusive device 100 as shown in FIGS. 8-10, illustrates an embodiment of the vaso-occlusive device in which the occlusive member 20 has a frame 118 which in its unexpanded state as shown in FIG. 8 and in an expanded state as shown in FIG. 10, is similar to an umbrella. The frame 118 has individual spokes 120 which in the expanded state support the canopy 122 of the umbrella-like structure.

Figure 11:
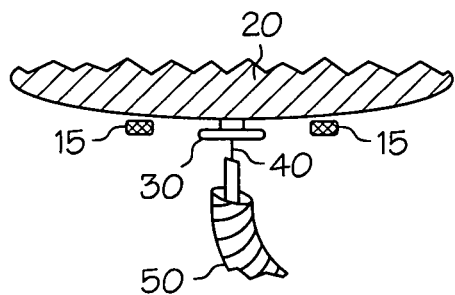
FIG. 11 is an expanded view of one embodiment of the securement member prior to deployment.
Figure 12:
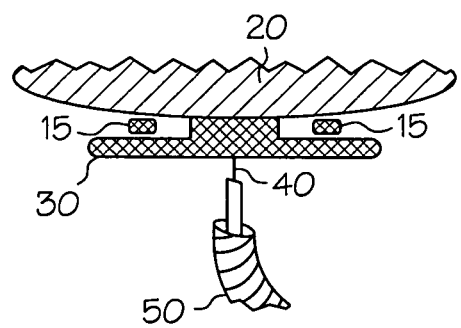
FIG. 12 is an expanded view of the same securement member as in FIG. 11 but in a deployed configuration.

FIG. 11 illustrates one embodiment of the securement member 30 of the vaso-occlusive device of the present invention in which securement member 30 is formed from a swellable material such as a hydrogel which swells upon exposure to an aqueous environment, or one with memory such as a compressed foam wherein the material returns to its original shape upon release from the microcatheter 50. In FIG. 11, securement member 30 is shown just released from microcatheter 50 and is not yet in its expanded configuration. Struts 15 are shown on either side of the securement member 30. FIG. 12 illustrates the same securement member 30 as in FIG. 11, but in a deployed configuration. Struts 15, are now located between occlusive member 20, which is now in an expanded configuration, and securement member 30, which is also in a deployed configuration. FIG. 12 shows the securement member 30 wherein it is anchored to the stent by "wrapping" itself around the stents struts 15 in its deployed state. Occlusive member 20, may also be formed from the same swellable material, or the same material having memory as securement member 30. It may also be formed of a different material.

Figure 13:
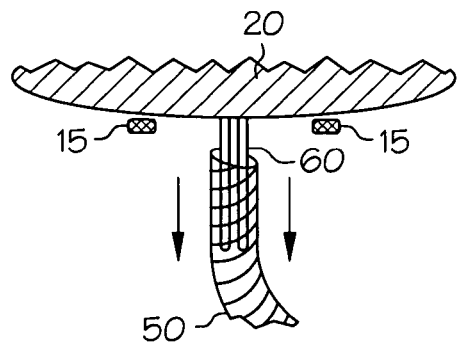
FIG. 13 illustrates an alternative embodiment of the securement member of the vaso-occlusive device of the present invention prior to release from the catheter.
Figure 14:
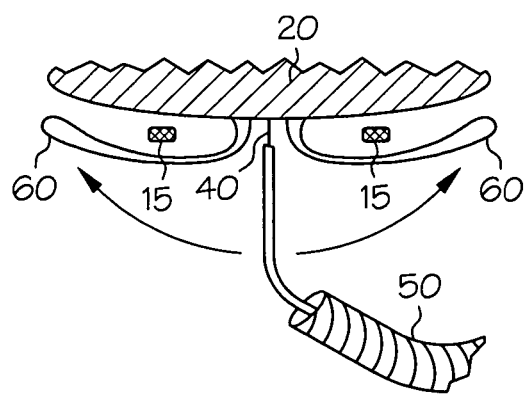
FIG. 14 illustrates the same securement member as shown in FIG. 13, but after release from the catheter.

FIG. 13 illustrates an alternative embodiment of the vaso-occlusive device of the present invention in which the securement member 30 is formed from strut-like elements 60 which are held inside microcatheter 50. The struts 15 may be leaf shaped (as shown) on a flattened helical form, or may be any shape which can be compressed to fit within a microcatheter and can expand to a shape which cannot fit through the openings in the strut 15. When microcatheter 50 is pulled back from stent 10, the strut-like elements 60, are released and open, laying flat against stent struts 15 as shown in FIG. 14. In this embodiment, strut-like elements 60 of securement member 30, may be formed of a shape memory material such as NITINOL®, or may be formed from a superelastic material.

Also visible in FIG. 14, is a severable junction 40 which is described above. Severable junction 40, in this embodiment, is shown in contact with occlusive member 20, as opposed to the embodiment shown in FIGS. 11 and 12, in which severable junction 40, is shown in contact with securement member 30.

Figure 15:
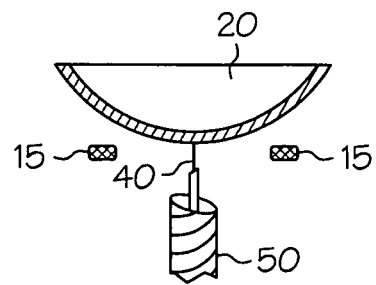
FIG. 15 illustrates another alternative embodiment wherein both the occlusive member and the securement member are formed of the same material.

FIG. 15 illustrates an embodiment of the vaso-occlusive device of the present invention in which both the occlusive member 20 and the securement member 30 are formed from a single material. In this embodiment, a material which swells upon exposure to an aqueous environment. Such materials include, for example, hydrogels, compressed foams, or the like. Swellable materials are discussed in more detail below. As shown in FIG. 15, both the occlusive member 20 and the securement member 30 have been released using the pusher wire, and they begin to swell. The vaso-occlusive device 100 is then brought down into the neck of the aneurysm such that the securement member 30 is on the opposite side of the stent struts 15 from the occlusive member 20. The swelling continues and the device blocks the aneurysm. The device is in its fully expanded configuration in FIG. 16. As can be seen from FIG. 16, the securement member 30 is on one side of the struts 15 and the occlusive member 20 is on the opposite side and actually in the aneurysm (not shown). In this manner, the securement member 30 anchors the vaso-occlusive device 100 to the stent.

Figure 17:
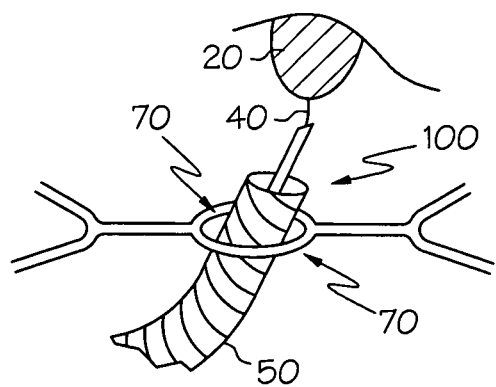
FIG. 17 illustrates a specialized opening which may be formed in a stent for accepting the vaso-occlusive device.

In another embodiment, rather than deploying the vaso-occlusive device 100 (only shown in partial view) through openings formed between stent struts, the stent may be made with a specialized opening 70 for accepting the vaso-occlusive device 100 of the present invention as shown in FIG. 17.

Figure 16:
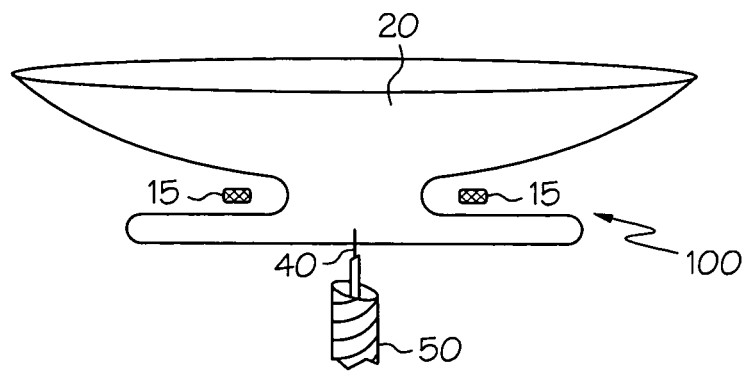
FIG. 16 illustrates the same device as shown in FIG. 15 with both the occlusive member and the securement member deployed.

Again, in FIGS. 15-17, a severable junction 40 is shown for detaching vaso-occlusive device 100 from catheter delivery device 50.

While in the embodiments described above, only one securement member has been employed in each embodiment, one or more securement members may be employed in the present invention. Securement members of any shape may be employed.

Further, support structures of any shape may be employed. For example, linear, Y-shaped, T-shaped stents, and so forth may be employed.

The occlusive portion of the device according to the present invention may be manufactured from any of a variety of materials including, but not limited to, polymeric materials. Examples of useful polymeric materials include both synthetic and natural materials. Further, the materials may be biocompatible and/or biodegradable materials. Examples of useful polymer materials include, but are not limited to, polyolefins including polyethylene and polypropylene, polyesters such as polyethyleneterephthalate (PET) and polybutylene terephthalate (PBT), polyurethanes, acrylics, polypeptides, polyethers, polyamides, fluoropolymers such as expanded polytetrafluoroethylene, and so on and so forth.

Swellable polymeric materials find utility herein. Such materials include those which are known to expand and become lubricious in aqueous fluids including, for example, a class of materials referred to generally as hydrogels may also be employed in the manufacture of the device according to the present invention. Such materials include hydrophilic, macroporous, polymeric, hydrogel foam material. Examples of such materials include, but are not limited, polyvinylpyrrolindone, polyethylene oxide and its copolymers with polypropylene oxide, polyacrylic acids, polyvinyl alcohols, hyaluronic acid, heparin, chondroitin sulfate, pectinic acid, carboxyl-derivatized polysaccharides, polyhydroxy ethyl methacrylate, polyacrylamide, hydrolyzed polyacrylonitriles, polymethacrylic acid, polyethylene amines, polysaccharides, and copolymers and combinations thereof, and so forth.

One particular example of a swellable material includes a swellable foam matrix formed as a macroporous solid is described in U.S. Pat. No. 5,750,585 which is incorporated by reference herein in its entirety. This material includes a foam stabilizing agent and a polymer or copolymer of a free radical polymerizable hydrophilic olefin monomer cross-linked with up to about 10% by weight of a multiolefin-functional cross-linking agent.

Naturally based materials or those which are biologically derived which find utility herein include, but are not limited to, collagen foams, harvested vascular material, films constructed from processed tissues, and so forth.

Shape memory materials are suitable for use in formation of the vaso-occlusive device of the present invention. Shape memory materials may be polymeric or metallic. Shape memory materials have the ability to remember their original shape, either after mechanical deformation, or by cooling and heating. Such materials are said to undergo a structural phase transformation. Typically, shape memory polymers (SMPs) are found to be segregated linear block co-polymers having a hard segment and a soft segment wherein the hard segment is crystalline, with a defined melting point, and the soft segment is amorphous, with a defined glass transition temperature. However, the hard segment may be amorphous and have a glass transition temperature rather than a melting point, and the soft segment may be crystalline and have a melting point rather than a glass transition temperature. The melting point or glass transition temperature of the soft segment is substantially less than the melting point or glass transition temperature of the hard segment. Some examples of shape memory polymers include, but are not limited to, those formed from polyethers, polyacrylates, polyamides, polysiloxanes, polyurethanes, polyether amides, polyurethane/ureas, polyether esters, urethane/butadiene copolymers, polynorbornenes, and mixtures thereof. See, for example, U.S. Pat. No. 5,506,300, U.S. Pat. No. 5,145,935, U.S. Pat. No. 5,665,822, and U.S. Pat. No. 6,388,043 each of which is incorporated by reference herein in its entirety.

Shape memory metals suitable for use herein include the alloys of TiNi (NITINOL®), CuZnAl, and FeNiAl, for example. These materials undergo a structure phase transformation referred to as a martensitic transformation.

Compressed foams may also be employed in the present invention because they have the ability to return to their original shape. Both open and closed cell foams may be employed. Materials satisfactory for use in compressed foams include, but are not limited to medical grade silicones and polyurethanes. As described above, natural materials such as collagens, may also be employed to make a compressed foam material.

Bioactive materials or materials having incorporated bioactive agents which facilitate aneurysm healing may also be employed in the construction of the device. Bioactive materials include agents which illicit a biological response within a patient. Such bioactive include therapeutic agents and drugs, for example. These agents may promote healing, tissue growth, cell growth, and so forth.

The vaso-occlusive device, in particular, the occlusive member, may be formed with a braided, woven, or mesh configuration.

Copolymers, and crosslinkable versions of the above described materials may also be suitable for use herein. And, of course, mixtures of the various materials described above may also be employed in the manufacture of the device according to the present invention.

A single material may be employed in forming both the occlusive member and the securement member, or different materials may be employed as described in some of the embodiments above. Additionally, one or more materials may be employed in forming only the occlusive member and/or the securement member. For example, in a further embodiment, the occlusive member may be formed of a combination of at least one polymeric material and at least one metal. In this embodiment, a metallic material such as a shape memory alloy, is employed to form the strut parts of an umbrella like structure which has an occlusive member similar to the canopy of an umbrella, and further has a frame including a plurality of spokes for providing support to the canopy. The canopy is formed of a polymeric material while the frame may be formed a metallic material or a polymeric material, for example. The frame and canopy have an expanded configuration and an unexpanded configuration for delivery.

The above lists of materials are intended for illustrative purposes only and are by no means exhaustive. One of ordinary skill in the art knows materials of the types described above.

The material from which the vaso-occlusive device is formed, or the vaso-occlusive device itself may be modified, or provided with additives, to make the vaso-occlusive device visible by conventional imaging techniques. For example, the device may be rendered visible using fluoroscopic techniques, rendered MRI visible, or both. This can be accomplished through the use of markers such as wire windings, marker bands, rivets, plugs, and so forth, or the radiopaque or MRI visible materials may be incorporated into the material from which the vaso-occlusive device is formed. Any suitable radiopaque or MRI visible material may be employed.

Suitable materials for providing radiopacity to the device include, but are not limited to, platinum, rhodium, palladium, rhenium, iridium, tantalum, tungsten, gold, silver, alloys of these metals, as well as polymeric materials with barium, for example. Radiopacity is desirable for visualization of the device for purposes of positioning the device at the site of the defect and to position inside the defect and for proper anchoring of the device.

The invention is further directed to the combination of a vaso-occlusive device having at least one securement member and a stent, where the at least one securement member is secured to the stent. Also, the invention is directed to the combination of a delivery catheter and a vaso-occlusive device having at least one securement member.

The invention is further directed to a method of occluding a vascular defect having an opening. The method comprises the steps of:
 a) deploying a support structure, as discussed above, to the vascular defect, the support structure having an opening for accepting a vaso-occlusive device;
 b) deploying a vaso-occlusive device having at least one occlusive member having an expanded configuration and an unexpanded configuration, as discussed above and at least one securement member, as discussed above, through the opening of the support structure and through the opening of the vascular defect into the vascular defect;
 c) expanding the at least one occlusive member; and
 d) anchoring the vaso-occlusive device to the support structure with the at least one securement member.

The invention is also directed to a method of closing and occluding an opening of an aneurysm from a parent blood vessel. The method comprises the steps of:
 a) deploying a support structure, as discussed above, at the site of the aneurysm, the support structure having at least one opening for accepting a vaso-occlusive device as discussed above, the vaso-occlusive device having at least one occlusive member which has an unexpanded configuration and an expanded configuration and at least one securement member, the support structure positioned at the opening of the aneurysm such that the at least one opening of the support structure is aligned with the opening of the aneurysm;
 b) deploying the vaso-occlusive device wherein the at least one occlusive member is in its unexpanded configuration, through the at least one opening of the support structure and the opening of the aneurysm and into the aneurysm;
 c) expanding the at least one occlusive member of the vaso-occlusive device to its expanded state whereby the vaso-occlusive device blocks the opening of the aneurysm from the parent blood vessel in its expanded state; and
 d) anchoring the vaso-occlusive device to the support structure with the at least one securement member.

The above disclosure is intended for illustrative purposes only and is not exhaustive. The embodiments described therein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A vaso-occlusive assembly, comprising:
 a stent defining an interior region and configured to be implanted in a blood vessel lumen across a neck opening of a vascular defect, and at least one occlusive member connected to at least one proximally extending securement member across a wall of the stent,
 wherein the at least one occlusive member and the at least one securement member are sized and shaped such that the at least one occlusive member and the at least one securement member are secured to the stent with the at least one occlusive member located outside of the stent interior region and the at least one securement member located within the stent interior region,
 wherein the at least one occlusive member is configured for insertion into the vascular defect by introduction through the interior region of the stent, exiting the stent between respective struts thereof, into the vascular defect, and wherein said at least one occlusive member of said vaso-occlusive device is in the shape of an umbrella-like canopy, parabola, or sphere
 wherein the at least one proximally extending securement member is configured to engage the respective stent struts as the occlusive member enters the vascular defect.

2. An assembly for the treatment of a vascular defect, said assembly comprising:
 a support structure defining an interior region and configured to be positioned transversely to a neck of the vascular defect; and
 at least one occlusive member connected to at least one securement member across a wall of the support structure,
 wherein the at least one occlusive member and the at least one securement member are sized and shaped such that the at least one occlusive member and the at least one securement member are secured to the support structure with the at least one occlusive member outside of the support structure interior region and the at least one securement member inside the support structure interior region,
 wherein the at least one occlusive member comprises an umbrella-like canopy, a parabola, or a sphere configuration having a continuous surface configured to bridge the neck of the vascular defect and substantially block the flow of fluid to said defect, and
 wherein the at least one securement member is configured to engage the support structure.

3. The assembly of claim 2, wherein said support structure is a stent or stent/graft.

4. The assembly of claim 3, wherein said support structure is a stent of the self-expanding variety.

5. The assembly of claim 2, wherein said at least one securement member, said at least one occlusive member, or both, are comprised of a metal or metal alloy.

6. The assembly of claim 5, wherein said metal is a shape memory metal.

7. The assembly of claim 2, wherein said at least one occlusive member, said at least one securement member, or both, are formed from a polymeric material.

8. The assembly of claim 7, wherein said polymeric material is selected from the group consisting of polyurethanes, polyolefins, polyesters, polyamides, fluoropolymers, silicones, acrylics, polypeptides, and mixtures thereof.

9. The assembly of claim 7, wherein said polymeric material is a swellable polymeric material which swells in an aqueous environment.

10. The assembly of claim 9, wherein said swellable polymeric material is a hydrogel.

11. The assembly of claim 2, wherein said at least one occlusive member, at least one securement member, or both, are formed from a biologically derived material.

12. The assembly of claim 11, wherein said biologically derived material is selected from the group consisting of collagen foams, harvested vascular material, processed tissues and combinations thereof.

13. The assembly of claim 2, wherein said at least one occlusive member is formed from a combination of at least one polymeric material and at least one metal or metal alloy.

14. The assembly of claim 2, wherein said at least one occlusive member and said at least one securement member are formed from a compressed foam.

15. The assembly of claim 2, wherein at least a portion of said at least one occlusive member has a braided, woven, knit, felt-like or mesh configuration.

16. The assembly of claim 2, further in combination with a catheter.

17. The assembly of claim 2, further comprising at least one radiopaque material.

18. The assembly of claim 2, further comprising at least one bioactive material.

19. A vaso-occlusive assembly, comprising:
a stent defining an interior region and configured to be positioned transversely to a neck of the vascular defect, and at least one occlusive member connected to at least one securement member across a wall of the stent, wherein the at least one occlusive member and the at least one securement member are sized and shaped such that the at least one occlusive member and the at least one securement member are secured to the stent with the at least one occlusive member located outside the stent interior region and the at least one securement member inside the stent interior region,
wherein the at least one occlusive member comprises an umbrella-like canopy, a parabola, or a sphere configuration,
wherein the at least one occlusive member and the at least one securement or both are formed from a swellable material or a compressed foam, and
wherein the at least one securement member is configured to engage respective struts of the stent.

* * * * *